US012806447B2

(12) United States Patent

Caskey et al.

(10) Patent No.: US 12,806,447 B2
(45) Date of Patent: Nov. 24, 2026

(54) SIMULTANEOUS FOCUSED ULTRASOUND AND fMRI AND APPLICATION OF FOCUSED ULTRASOUND OUTSIDE OF MRI ENVIRONMENT

(71) Applicant: Vanderbilt University, Nashville, TN (US)

(72) Inventors: Charles F. Caskey, Nashville, TN (US); Limin Chen, Nashville, TN (US); William A. Grissom, Nashville, TN (US); Peter E. Konrad, Nashville, TN (US); Benoit M. Dawant, Nashville, TN (US); Willliam J. Rodriguez, Nashville, TN (US)

(73) Assignee: Vanderbilt University, Nashville, TN (US)

( * ) Notice: Subject to any disclaimer, the term of this patent is extended or adjusted under 35 U.S.C. 154(b) by 104 days.

(21) Appl. No.: 18/029,247

(22) PCT Filed: Oct. 8, 2021

(86) PCT No.: PCT/US2021/054247
§ 371 (c)(1),
(2) Date: Mar. 29, 2023

(87) PCT Pub. No.: WO2022/076870
PCT Pub. Date: Apr. 14, 2022

(65) Prior Publication Data

US 2023/0398380 A1 Dec. 14, 2023

Related U.S. Application Data

(60) Provisional application No. 63/089,977, filed on Oct. 9, 2020.

(51) Int. Cl.
*A61N 7/02* (2006.01)
*A61B 90/11* (2016.01)
(Continued)

(52) U.S. Cl.
CPC ................ *A61N 7/02* (2013.01); *A61B 90/11* (2016.02); *A61B 90/14* (2016.02); *A61N 2007/0021* (2013.01)

(58) Field of Classification Search
None
See application file for complete search history.

(56) References Cited

U.S. PATENT DOCUMENTS

2005/0215899 A1* 9/2005 Trahey ................ A61B 5/0048 600/439
2013/0331685 A1 12/2013 Liu et al.
(Continued)

OTHER PUBLICATIONS

M. A. Phipps et al., "Considerations for Ultrasound Exposure During Transcranial MR Acoustic Radiation Force Imaging." Scientific Reports, Nature research, 9:16235, 2019.
(Continued)

*Primary Examiner* — Shahdeep Mohammed
(74) *Attorney, Agent, or Firm* — Blank Rome LLP

(57) ABSTRACT

A workflow has been developed that enables initially mapping of a focused ultrasound (FUS) beam using magnetic resonance (MR) thermometry or MR-acoustic radiation force imaging (MR-ARFI) while working within the MRI device. During this procedure, key measurements will be taken including the precise location of the transducer relative to the skull and the transducer parameters (such as amplitudes and phases) required to place the ultrasound focus at the desired focal size and location in the skull. The anatomical measurements will be used to build a patient-specific, device-specific stereotactic frame to hold the transducer in the position relative to the skull and the aberration corrects will be applied. FUS therapy can then be delivered to the patient outside of the MR environment.

14 Claims, 8 Drawing Sheets

(51) Int. Cl.

| | |
|---|---|
| ***A61B 90/14*** | (2016.01) |
| *A61N 7/00* | (2006.01) |

(56) References Cited

U.S. PATENT DOCUMENTS

| | | | | |
|---|---|---|---|---|
| 2014/0350439 | A1 | 11/2014 | Zur et al. | |
| 2017/0291044 | A1 | 10/2017 | Zheng et al. | |
| 2018/0192990 | A1 | 7/2018 | Tanter et al. | |
| 2019/0029650 | A1 | 1/2019 | Parker et al. | |
| 2020/0008783 | A1 | 1/2020 | Bolster, Jr. et al. | |
| 2020/0205782 | A1 * | 7/2020 | Vortman | A61N 7/02 |
| 2021/0212743 | A1 * | 7/2021 | Li | G16H 50/50 |

OTHER PUBLICATIONS

J. Chen et al., "Optimization of Encoding Gradients for MR-ARFI." Magnetic Resonance in Medicine, 63:1050-1058, 2010.
G. Maimbourg et al., "3D-Printed Adaptive Acoustic Lens as a Disruptive Technology for Transcranial Ultrasound Therapy Using Single-Element Transducers." Physics in Medicine & Biology, 63, 025026, 2018.
M. Fink et al., Time Reversal Acoustics. IEEE Ultrasonics Symposium, vol. 2, pp. 850-859, 2004.
E. Kaye et al., "Rapid MR-ARFI Method for Focal Spot Localization During Focused Ultrasound Therapy." Magnetic Resonance in Medicine, vol. 65, pp. 738-743, 2011.
International Search Report corresponding to PCT/US2021/054247 dated Dec. 29, 2021.

* cited by examiner

Increasing Input Power →

| | | | | |
|---|---|---|---|---|
| PNP (Free) | Control | 1.68 MPa | 2.25 MPa | 2.81 MPa |
| PNP (De-rated) | – | 0.54 MPa | 0.72 MPa | 0.90 MPa |
| MI (Free) | – | 1.88 | 2.51 | 3.14 |
| MI (De-rated) | – | 0.60 | 0.80 | 1.01 |

SIMULTANEOUS FOCUSED ULTRASOUND AND fMRI AND APPLICATION OF FOCUSED ULTRASOUND OUTSIDE OF MRI ENVIRONMENT

CROSS REFERENCE TO RELATED APPLICATION(S)

This application is a national stage entry under 35 U.S.C. § 371 of PCT/US2021/054247, filed on Oct. 8, 2021, which claims priority to U.S. Provisional Patent Application Ser. No. 63/089,977, filed on Oct. 9, 2020. The contents of these applications are hereby incorporated herein by reference in their entirety.

GOVERNMENT SPONSORSHIP

This invention was made with government support under Grant No. 1U18EB029351-01 awarded by NIH. The government has certain rights in the invention.

FIELD OF THE INVENTION

Embodiments are in the field of focused ultrasound and magnetic resonance imaging (MRI). More particularly, embodiments disclosed herein relate to simultaneous focused ultrasound and functional MRI (fMRI) and application of focused ultrasound outside of a MRI environment.

BACKGROUND

Neuromodulation is the process of directly stimulating the brain with the goal of modulating activity through excitation or inhibition. Traditional methods of neuromodulation are either highly invasive and precise (deep brain stimulation (DBS), direct electrode) or noninvasive with poor spatial resolution (transcranial magnetic stimulation (TMS), transcranial direct current stimulation (TDCS)). The invasiveness of therapies can limit their application, since surgeons or patients may be hesitant to undergo a highly invasive procedure with unknown efficacy, while the spatial precision of non-invasive methods limit their efficacy. Ultrasound can modulate neural activity and is being increasingly explored as a neuromodulation method that is both non-invasive and spatially precise. By focusing energy through a transducer, ultrasonic energy can be concentrated to small regions in the skull, including deep brain regions. The direct action of ultrasound on the brain has been shown to elicit action potentials in different kinds of neurons, while acoustically activated particles are being leveraged to deliver anesthetics to specific regions of the brain or open the blood brain barrier for gene delivery. These exciting developments can serve as neuro-investigative tools as well as many potential medical applications in neuropsychiatry and neurosurgery.

Challenges with image-guidance and integration to MM machines must be overcome to fully leverage focused ultrasound (FUS) neuromodulation of any kind. Improved MR imaging during FUS procedures will be crucial for mapping the brain during FUS procedures. Current technologies rely on volume imaging MR coils to acquire images of the brain during FUS procedures. Although these coils are sufficient for thermometry during thermal ablation, the volume coils do not provide high enough signal-to-noise ratio (SNR) or parallel imaging capabilities for functional MM. The MR coil designs described in this disclosure will allow for fast, low-distortion, high SNR imaging while still being able to precisely deliver FUS to targets for any neuromodulation purpose. A second major challenge with FUS neuromodulation is image-guidance. The gold standard for accuracy is to map effects of heat or acoustic radiation force-induced displacement caused by ultrasound with the MRI. Those measurements incorporate aberrations that are known to occur in the skull, but the requirement of being within the MR environment is a major barrier for routine use of FUS neuromodulation. Currently, researchers use optical tracking or stereotactic methods to place the ultrasound transducer relative to the head, but those methods are known to have error on the order of 2-3 mm under ideal circumstances. When factoring in aberration due to the skull, those methods will be less accurate.

Thus, it is desirable to provide a method for simultaneous focused ultrasound and fMRI and application of focused ultrasound outside of an MRI environment that is able to overcome the above disadvantages and which provides a workflow that enables FUS delivery to occur outside of the MRI environment with better accuracy and dosimetry than other available methods.

Advantages of the present invention will become more fully apparent from the detailed description of the invention hereinbelow.

SUMMARY OF THE INVENTION

Embodiments are directed to a method for applying focused ultrasound (FUS) to a patient. The method includes: mapping a FUS beam in a patient inside a magnetic resonance (MR) environment; building a patient-specific stereotactic frame using data obtained from the mapping; and delivering FUS therapy to the patient using the patient-specific stereotactic frame.

Embodiments are also directed to a system that applies focused ultrasound (FUS) to a patient. The system includes: a patient-specific stereotactic frame configured as being built using data obtained from mapping of a FUS beam in a patient inside a magnetic resonance (MR) environment; and a FUS transducer configured to deliver FUS therapy to the patient using the patient-specific stereotactic frame. The patient-specific stereotactic frame is anchored between the patient and the FUS transducer that delivers the FUS therapy.

Additional embodiments and additional features of embodiments for the method and system for applying focused ultrasound (FUS) to a patient, are described below and are hereby incorporated into this section.

BRIEF DESCRIPTION OF THE DRAWINGS

The foregoing summary, as well as the following detailed description, will be better understood when read in conjunction with the appended drawings. For the purpose of illustration only, there is shown in the drawings certain embodiments. It is understood, however, that the inventive concepts disclosed herein are not limited to the precise arrangements and instrumentalities shown in the figures. The detailed description will refer to the following drawings in which like numerals, where present, refer to like items.

FIG. 1A illustrates a map of the full simulation grid with the transducer location represented in yellow at the top and the skull fragment CT which was used to generate the medium properties. FIGS. 1B-1D illustrate peak pressure maps for three intersecting planes at the focus location;

FIG. 2A illustrates the thermal simulation grid with a pressure map overlay. FIG. 2B illustrates a map of the temperature at the focus target increased by less than 0.1 °C. FIG. 2C illustrates a map of the voxel with the largest temperature change in the simulation;

FIG. 3A illustrates a spherically-focused single-element FUS transducer (gray) used to sonicate a tissue-mimicking brain phantom (purple). FIGS. 3B-3C illustrate a demonstration of how the location of the transducer was obtained via optical tracking and used to align the MR-ARFI motion-encoding gradients (MEGs) with the FUS propagation direction (Gus);

FIG. 4A illustrates MR-ARFI displacement maps for an oblique rotation of the FUS transducer. FIG. 4B illustrates the mean displacement measured by MR-ARFI at the focus for each MEG orientation and each transducer rotation;

FIG. 5A illustrates displacement images obtained with the an optically tracked MR-ARFI pulse sequence in vivo, and the peak transcranial displacement is plotted in FIG. 5B;

FIG. 7A illustrates a representative in vivo brain temperature map that shows that no significant temperature rise could be detected using acoustic parameters designed for MR-ARFI. FIG. 7B illustrates the brain temperature time course map at the acoustic focus (red) and near the skull (green);

DETAILED DESCRIPTION OF THE INVENTION

Figures 1A, 1B, 1C, 1D:
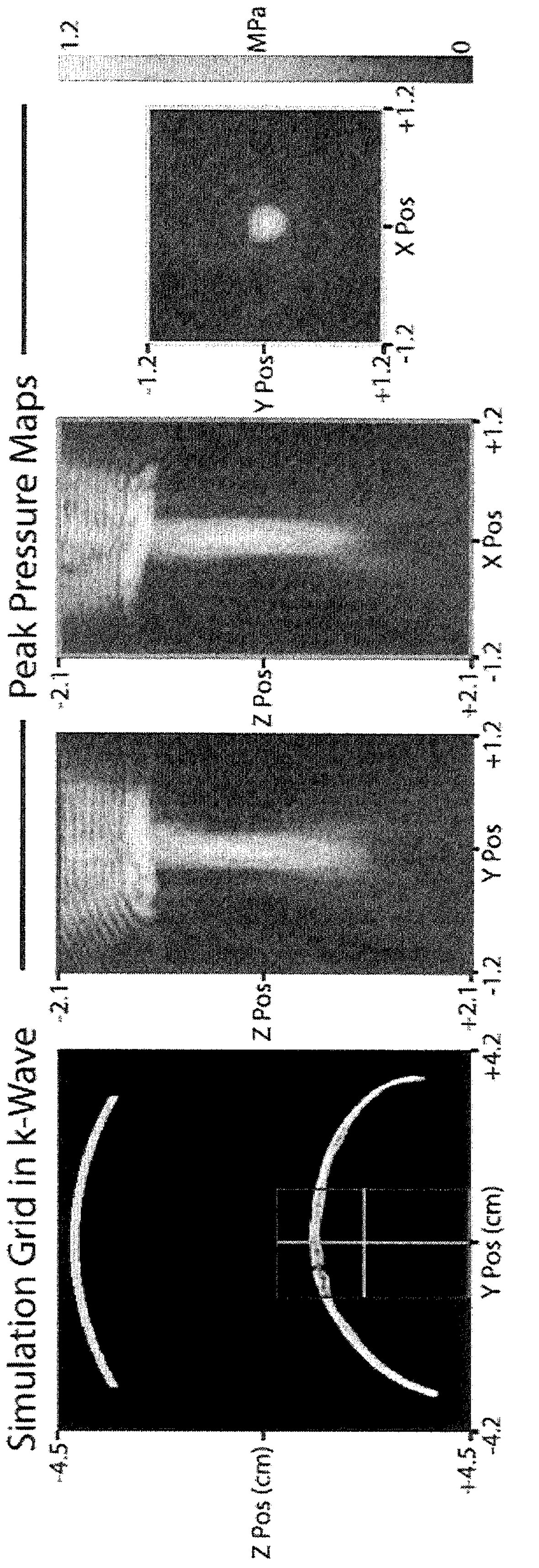
FIGS. 1A-1D are drawings illustrating maps of pressure simulation with an ex vivo skull fragment.

It is to be understood that the figures and descriptions of the present invention may have been simplified to illustrate elements that are relevant for a clear understanding of the present invention, while eliminating, for purposes of clarity, other elements found in a typical MR thermometry device, MR-acoustic radiation force imaging (MR-ARFI) device, or FUS device, or typical method of using any of those devices. Those of ordinary skill in the art will recognize that other elements may be desirable and/or required in order to implement the present invention. However, because such elements are well known in the art, and because they do not facilitate a better understanding of the present invention, a discussion of such elements is not provided herein. It is also to be understood that the drawings included herewith only provide diagrammatic representations of the presently preferred structures of the present invention and that structures falling within the scope of the present invention may include structures different than those shown in the drawings. Reference will now be made to the drawings wherein like structures are provided with like reference designations.

Before explaining at least one embodiment in detail, it should be understood that the inventive concepts set forth herein are not limited in their application to the construction details or component arrangements set forth in the following description or illustrated in the drawings. It should also be understood that the phraseology and terminology employed herein are merely for descriptive purposes and should not be considered limiting.

It should further be understood that any one of the described features may be used separately or in combination with other features. Other invented devices, systems, methods, features, and advantages will be or become apparent to one with skill in the art upon examining the drawings and the detailed description herein. It is intended that all such additional devices, systems, methods, features, and advantages be protected by the accompanying claims.

To address the challenge of using FUS neuromodulation outside of the MM environment, a workflow has been developed that enables initially mapping of the FUS beam using MR thermometry or MR-acoustic radiation force imaging (MR-ARFI) while working within the MRI device. During that procedure, key measurements will be taken including the precise location of the transducer relative to the skull and the transducer parameters (such as amplitudes and phases) required to place the ultrasound focus at the desired focal size and location in the skull (achieved electronically via ultrasound steering or with an ultrasound lens). The anatomical measurements will be used to build a patient-specific, device-specific stereotactic frame to hold the transducer in the position relative to the skull and the aberration corrections will be applied. FUS therapy can then be delivered to the patient outside of the MR environment.

In particular, embodiments of the present disclosure may employ the following workflow steps which achieve the aforementioned advantages:

1) Map a FUS beam in a patient inside a MR environment using MR thermometry or MR-ARFI, including:
   a. Record a (e.g., optimum) location of a FUS transducer relative to the patient during mapping;
   b. Record (e.g., optimum) ultrasound parameters (e.g., amplitude, frequency, phase, duty cycle, focal position, f-number, and/or power delivered to transducer);
   c. Calculate FUS aberration corrections; and
   d. Record radiofrequency (RF) echo signals from the FUS transducer as a signature of transducer position relative to the head/skull and acoustic coupling;
2) Use the recorded information (in steps 1a, 1b, and 1d) and the calculated FUS aberration corrections described above to build a patient-specific, ultrasound-specific stereotactic frame; and
3) Deliver FUS therapy to the patient inside or outside the MR environment using the patient-specific, ultrasound-specific stereotactic frame.

The minimal experiment to demonstrate feasibility of the technology outlined in this disclosure would be to show that the invention can target a relevant location within a human skull from a cadaver within and outside of the MM. The skull will be filled with a tissue-mimicking material and a small sensor at a target location within the skull. The procedure would begin by placing the transducer relative to the head within the MRI using optical tracking and a normal positioning device. Within the MRI, the acoustic beam will be visualized using MR-ARFI or MR thermometry and adjustments will be made to the beam location using an aberration correction algorithm. The combined MM coil and ultrasound transducer development disclosed here would allow for this part of the experiment to be done at an acoustic dose below levels that cause significant detrimental bioeffects in brain tissue and which is lower than currently possible with volume coils. During this procedure, the location of the transducer will be unambiguously defined relative to the skull using standard rigid or non-rigid registration methods (e.g., by using MR-visible fiducial-based registration markers). That positioning will be replicated outside of the MR environment using, for example, a stereotactic frame (e.g., of the type similar to those that have been previously developed by FHC Incorporated). The previously computed aberration correction methods will be used to apply focused ultrasound at the desired location within the skull, outside of the MR environment. This overall experiment will demonstrate better imaging metrics in the presence of FUS and accurate placement of an acoustic beam outside of the MR environment.

The invention has at least the following advantages over current methods used for ultrasound neuromodulation:

1. The improved imaging enables ARFI-based phase correction to be performed within the magnet (i.e., MR device);
2. Applying these validated ultrasound phase delays outside of the MM with a transducer-bearing stereotactic frame allows for high accuracy therapy outside of the MRI environment. That capability enables repeated therapy without repeated MR-guided image guidance sessions. Current methodologies only achieve ~3 mm accuracy, whereas the proposed stereotactic frame solution is less than 3 mm in accuracy. Such positioning accuracy is required for aberration correction to work;
3. RF pulse echo ultrasound imaging or other transmit-receive scheme (e.g. transmitting from one ultrasound transducer and receiving on another) can provide confirmation that acoustic coupling within the magnet and outside the magnet are similar; and
4. Increased SNR during fMRI+FUS enables identification of important brain regions for therapeutic application.

Some of the novel elements of the invention are as follows:

1. Development of an MR coil and transducer that can work together to achieve simultaneous focal stimulation in the brain;
2. A bone-anchored design that maintains high accuracy and does not interfere acoustically; and
3. A process for precisely delivering FUS to a target within a brain within and outside of the MRI environment.

Embodiments of the present disclosure require an MRI, MR environment, and US delivery. The invention relies on MR acoustic radiation force imaging (MR-ARFI) and MR-thermometry as the gold standard for positioning, which requires applying a small acoustic dose within the magnet during the calibration step. That dosage would need to remain in the non-therapeutic regime.

The current clinical standard for aberration correction (which is necessary for the workflow/process described herein to function) requires a CT, which limits the use of the system to patients or study members who can receive a CT scan. Testing of healthy subjects would not be recommended if CT was required. Other validated non-CT aberration correction methods rely on MR-ARFI or MR thermometry.

Overall, the inventors believe this technology will overcome major challenges faced in the field of ultrasound neuromodulation: targeting the brain while maintaining high image quality, simultaneous fMRI and ultrasound neuromodulation, and the ability to function within and outside of the MRI environment. The latter is especially important and enabling of treatments that require repeated intervention, which is common for neuromodulation-based therapy.

Embodiments of the present disclosure may employ any or all of the following considerations for ultrasound exposure during transcranial MR-ARFI:

An aim of this study was to improve the sensitivity of MR-ARFI to minimize pressures required to localize FUS beams, and to establish safe FUS localization parameters for ongoing ultrasound neuromodulation experiments in living non-human primates, and which is also applicable to humans. The inventors developed an optical tracking method to ensure that the MR-ARFI motion-encoding gradients (MEGs) were aligned with a single-element FUS transducer and that the imaged slice was prescribed at the optically tracked location of the acoustic focus. That method was validated in phantoms, which showed that MR-ARFI-derived displacement sensitivity is maximized when the MR-ARFI MEGs were maximally aligned with the FUS propagation direction. The method was then applied in vivo to acquire displacement images in two healthy macaque monkeys (*M fascicularis*) which showed the FUS beam within the brain. Temperature images were acquired using MR thermometry to provide an estimate of in vivo brain temperature changes during MR-ARFI, and pressure and thermal simulations of the acoustic pulses were performed using the k-Wave package which showed no significant heating at the focus of the FUS beam. The methods presented here will benefit the multitude of transcranial FUS applications as well as future human applications.

Researchers have known that ultrasound can affect neuronal activity for nearly a century and are increasingly exploring focused ultrasound (FUS) for neuromodulation, which is defined as reversible stimulation inhibition, modification and therapeutic alteration. Transcranial thermal ablation with high intensity focused ultrasound is a mature technology with FDA approval for non-invasive ablative thalamotomy procedures in patients. Pulsed-wave FUS at relatively low acoustic intensities is being developed as a research tool for non-invasive neuromodulation, with the ability to both stimulate and suppress neuronal activity through an intact skull. In addition to the direct effects of FUS neuromodulation, researchers are using FUS to locally deliver neuromodulatory drugs, transiently open the blood brain barrier, or deliver genetic vectors capable of modulating neural activity in spatially selective regions.

Prior to applying FUS, knowledge of the location of the acoustic focus must be obtained to verify that the ultrasound beam is reaching its intended target. For ablative procedures, small temperature rises in the target tissue tracked with MR thermometry pulse sequences have been used to determine where the FUS beam is within the brain. However, off-target heating in the near- and far-fields of the ultrasound transducer can have deleterious effects and human brain function is known to be sensitive to fluctuations in brain temperature. Given these concerns, a beam localization method that does not rely on temperature increases is desirable for FUS applications. Optical tracking has been used to target the FUS beam. That method does not require any energy to be deposited in the brain but suffers from registration errors and does not account for aberrations induced by the skull. Simulations of the FUS transmitting through the skull can be performed with CT-derived acoustic property maps to estimate the focus location. However, those parameter maps are both subject skull-specific and also depend on the X-ray energy and reconstruction kernel of the measured Hounsfield units (HU). Additionally, accurate simulations can require long computation times.

MR-acoustic radiation force imaging (MR-ARFI) pulse sequences can localize the acoustic focus prior to FUS procedures. In MR-ARFI, motion-encoding gradients are used to encode the tissue displacement response to a short ultrasound excitation (≈ms) into the phase of an MR image. The acoustic radiation force is proportional to the local acoustic intensity of the ultrasound beam, so monitoring displacement via MR-ARFI provides a non-invasive tool to both localize the acoustic focus and to calibrate beam intensity. Unlike current beam localization methods, which predict the focus location based on simulations that are registered to the experiment, MR-ARFI is non-parametric and does not require a priori knowledge of skull acoustic properties, but rather can localize the beam in situ prior to any FUS application. MR-ARFI-derived displacement measurements have been validated in small animal in vivo studies, with ultrasound imaging-derived measurements as the gold standard. Also, ex vivo studies in human cadavers have shown that sufficient sensitivity to displacement can be achieved beyond an intact skull with MR-ARFI using commercial transcranial FUS transducers.

In FUS applications like neuromodulation where the target tissue should not be affected by the beam localization procedure, MR-ARFI is constrained by the potential accumulation of ultrasound energy in the target tissue, which can have unwanted bioeffects. Broadly, interactions of ultrasound with tissue can be divided into either thermal or non-thermal mechanisms. As ultrasound waves propagate through tissue, some energy is attenuated and absorbed in the form of heat, depending on factors like the local acoustic intensity, frequency, exposure time, and tissue type. That is especially relevant for transcranial applications of ultrasound on living subjects since their skulls are covered by skin, soft tissue and muscle. It is known that the attenuation coefficient of skull bone (up to 20 dB $cm^{-1}$ $MHz^{-1}$) is many times that of brain tissue (approximately 0.6 dB·$cm^{-1}$ $MHz^{-1}$). Ultrasound also interacts with tissue via non-thermal mechanical interactions. Pressure waves with high rarefactional (negative) amplitudes can draw dissolved gas out of liquid tissue, forming cavitation bubbles. Cavitation bubbles may expand and contract with small-amplitude oscillations (stable cavitation), but in some cases, they may rapidly collapse and produce shock waves (inertial cavitation), which can lead to tissue damage. While safety limits have been proposed in the context of diagnostic ultrasound imaging applications, they likely do not encompass the range of biological phenomena that may occur in response to pulses commonly used during MR-ARFI. To safely implement MR-ARFI, thermal and mechanical bioeffects must be avoided while applying high enough ultrasound intensity to generate detectable displacements. A goal of the present study is to detect and visualize the transcranial FUS beam with MR-ARFI and ultimately establish a framework to understand potential bioeffects based on simulations and experimental observations.

The inventors implemented transcranial MR-ARFI in living non-human primates informed by simulations of pressure fields and thermal deposition in the skull and brain. To maximize displacement sensitivity, the inventors developed an optical tracking method to ensure that the MR-ARFI motion-encoding gradients are aligned with the FUS propagation direction and with the imaged slice prescribed at the optically tracked location of the acoustic focus. The methods described here address the need to determine the precise location of the FUS's interaction with brain tissue during transcranial FUS stimulation. The inventors present these methods in the context of minimizing FUS exposure during FUS neuromodulation, where freely moveable transducers are increasingly used creating a need to image the estimated focal location with MR-ARFI and determine the gradient direction that will minimize exposure. The techniques and bioeffects considerations presented here are generally applicable to all transcranial FUS procedures.

Results

Skull attenuation and pressure field simulations. Measurements of the FUS transducer output were acquired with and without an ex vivo skull present to characterize attenuation expected in the skull. The mean detected pressures at 802 kHz in the water tank were 284 kPa (free-field) and 91 kPa (skull fragment present). With the skull fragment, 32.1% of the free-field pressure was recorded at the same location beyond the skull. Simulations of the same FUS pulses used during subsequent MR-ARFI showed a maximum pressure at the target of 1.14 MPa and a maximum pressure in the skull of 3.19 MPa (FIG. 1, note the color map is scaled to emphasize the focus in the brain). Since the highest pressure is in the skull, which absorbs more sound than tissue, thermal simulations show the most heating in the skull (FIG. 2). A 100-sonication simulation of an ARFI pulse resulted in a maximum heating in the skull of 2.22 °C and a maximum heating at the target of 0.05 °C. The heating in the skull approached a steady state; however, at the focus, the heating did not appear to be in a steady state. An additional pressure simulation matched to the conditions of the water tank experiment resulted in a free field simulated pressure of 284 kPa and transcranial pressure of 118.5 kPa. That simulation showed 41.73% transmission through the ex vivo skull fragment.

FIGS. 1A-1D are drawings illustrating maps of pressure simulation with an ex vivo skull fragment. FIG. 1A illustrates a map of the full simulation grid with the transducer location represented in yellow at the top and the skull fragment CT which was used to generate the medium properties. The inset boxes in FIG. 1A are where thermal simulations were performed. FIGS. 1B-1D illustrate peak pressure maps for three intersecting planes at the focus location. The highest pressure was within the skull itself, but the pressure maps are saturated to better show the focus. The maximum pressure at the focus target was 1.14 MPa and the maximum pressure within the skull was 3.19 MPa.

Figure 2A:
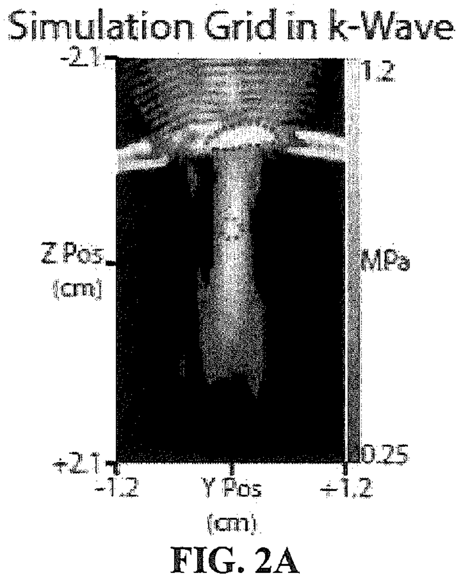
FIGS. 2A-2C are drawings illustrating maps of thermal simulation results of 100 MR-ARFI sonications.
Figure 2B:
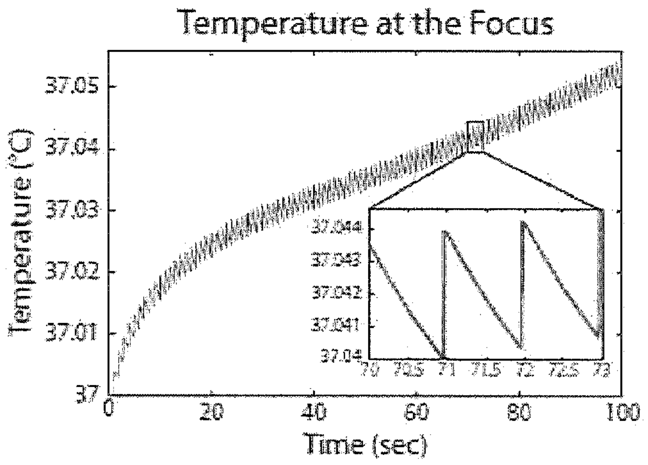
Figure 2C:
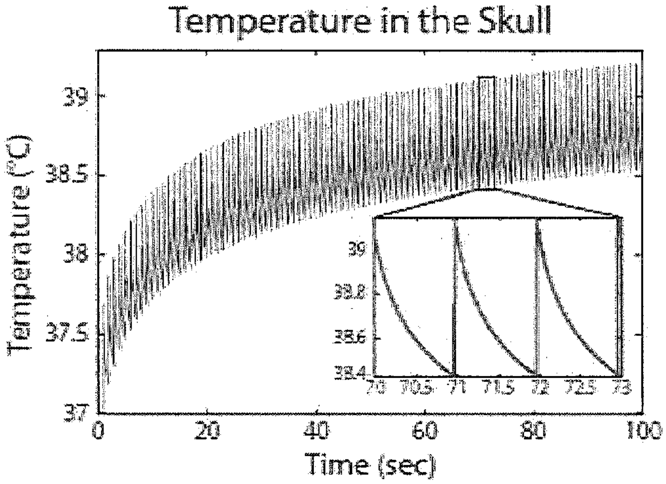

FIGS. 2A-2C are drawings illustrating maps of thermal simulation results of 100 MR-ARFI sonications. FIG. 2A illustrates the thermal simulation grid with a pressure map overlay. The pressure map is threshold-limited to only show values above 0.5 MPa. The red circle shows the approximate target location and the blue outline shows the maximal heating area reported in the skull. FIG. 2B illustrates a map of the temperature at the focus target increased by less than °C. The target was located at the intersection of the three slices in (A). FIG. 2C illustrates a map of the voxel with the largest temperature change in the simulation. That voxel is located within the skull as expected due to the much higher acoustic absorption and pressure. That simulation showed a temperature change within the skull of up to 2.2 °C.

Aligning MR-ARFI MEGs with FUS propagation direction improves sensitivity. To test whether optical tracking could predict MEG angle, the inventors placed the transducer at varied angles relative to MEG direction and applied sound to a phantom known to absorb sound and deform similarly to tissue (FIG. 3). Displacement maps acquired in the agar and graphite phantom using the inventors' optically tracked MR-ARFI pulse sequence in each MEG and transducer/phantom orientation show micron-scale displacement at the expected location of the ultrasound focus (FIG. 4A). FIG. 4B reports mean focal displacements in a 3×3 pixel ROI at the focus for each MEG and transducer orientation pair. In every transducer orientation, the measured displacement was highest when the MEGs were prescribed along the FUS propagation direction using the optical tracking method. At matched acoustic output, the range of detected displacements was low when MEGs were prescribed via optical tracking (1.33-1.41 μm; mean±SD=1.37+0.04 μm), suggesting that the optically-tracked alignment of the MEG can be used to improve SNR.

Figure 3A:
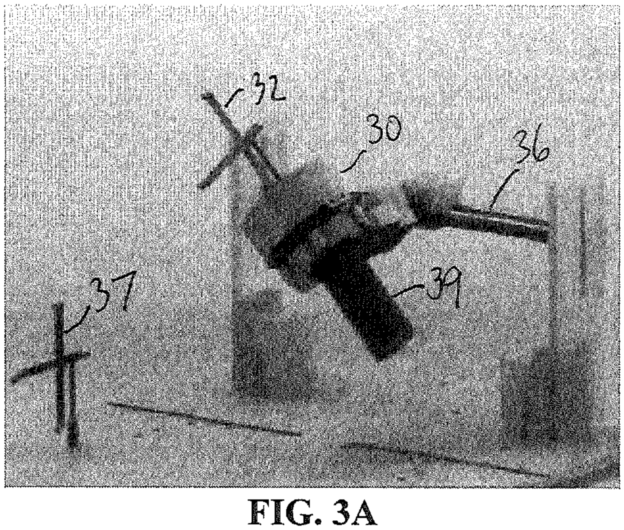
FIGS. 3A-3C are drawings illustrating targeting with an optically tracked FUS transducer.
Figure 3B:
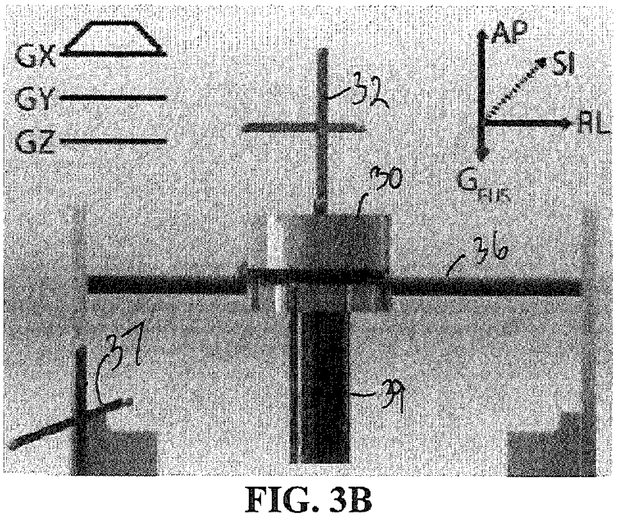
Figure 3C:
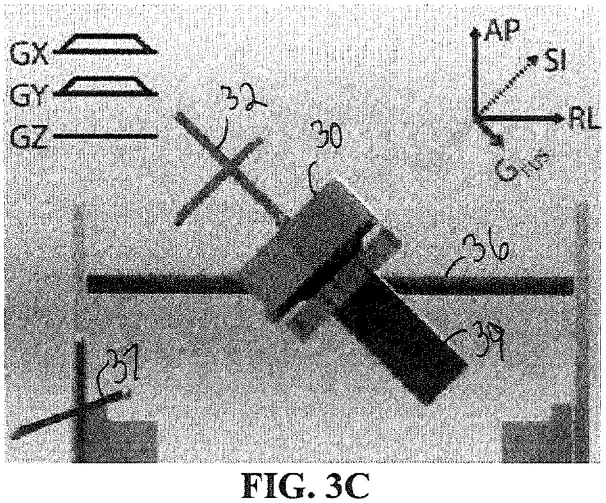
Figure 4A:
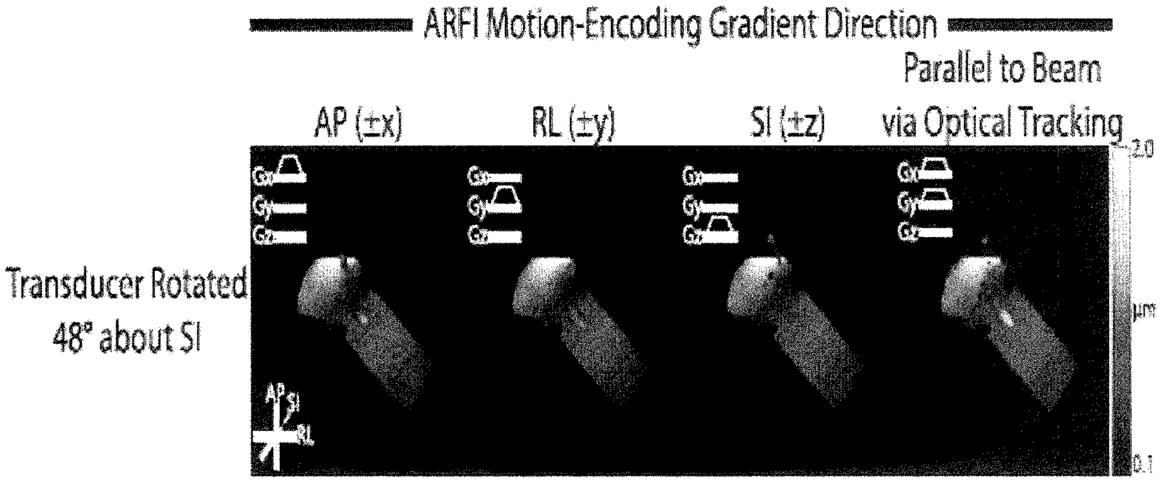
FIGS. 4A-4B are drawings illustrating optical tracking-based alignment of MR-ARFI motion-encoding gradients (MEGs) with the FUS propagation direction in a phantom.
Figure 4B:
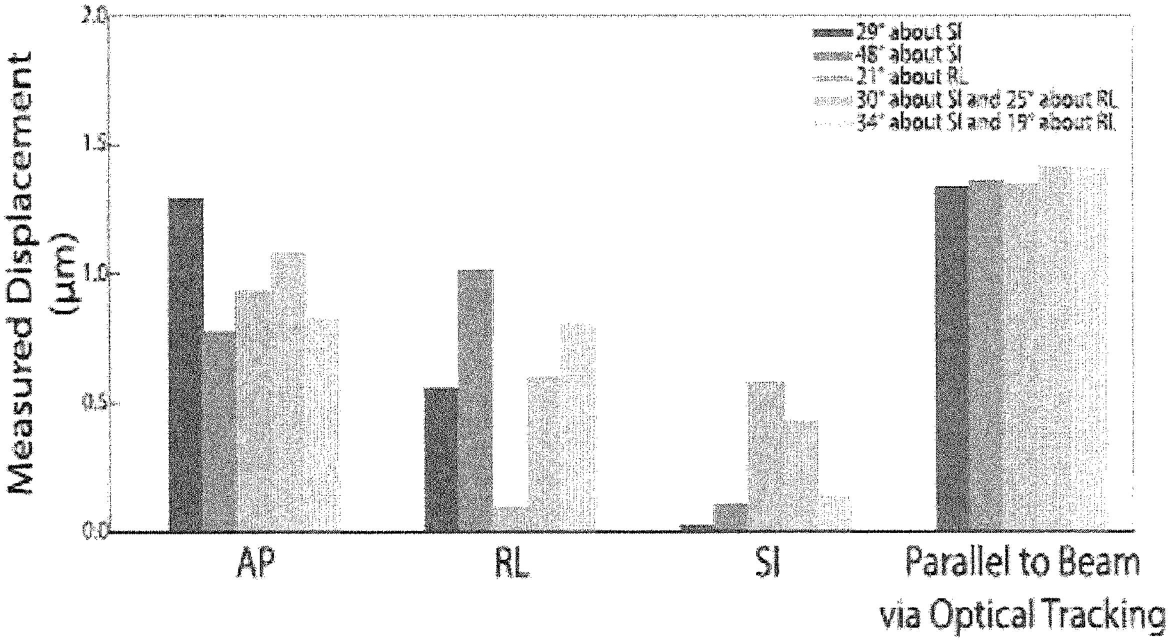

FIGS. 3A-3C are drawings illustrating targeting with an optically tracked FUS transducer. FIG. 3A illustrates a spherically-focused single-element FUS transducer (30) used to sonicate a tissue-mimicking brain phantom (39). An MRI-compatible rigid body tracker was mounted to the patient bed (37), and another body tracker was mounted to the transducer (32). As shown, the phantom mold was rigidly attached to the transducer housing. The transducer-phantom apparatus was mounted on a three-axis stereotactic frame (36) so that sonications could be performed in any physical orientation. FIGS. 3B-3C illustrate a demonstration of how the location of the transducer was obtained via optical tracking and used to align the MR-ARFI motion-encoding gradients (MEGs) with the FUS propagation direction ($G_{FUS}$).

FIGS. 4A-4B are drawings illustrating optical tracking-based alignment of MR-ARFI motion-encoding gradients (MEGs) with the FUS propagation direction in a phantom. FIG. 4A illustrates MR-ARFI displacement maps for an oblique rotation of the FUS transducer. Maps were shown with the MEGs prescribed along the cardinal axes and along the optical tracking determined propagation direction. FIG. 4B illustrates a map of mean displacement measured by MR-ARFI at the focus for each MEG orientation and each transducer rotation. The highest mean displacement is detected when the MEG is aligned with the FUS propagation direction obtained via optical tracking. Mean focal displacement was computed in a 3×3 px ROI at the acoustic focus.

Figure 5A:
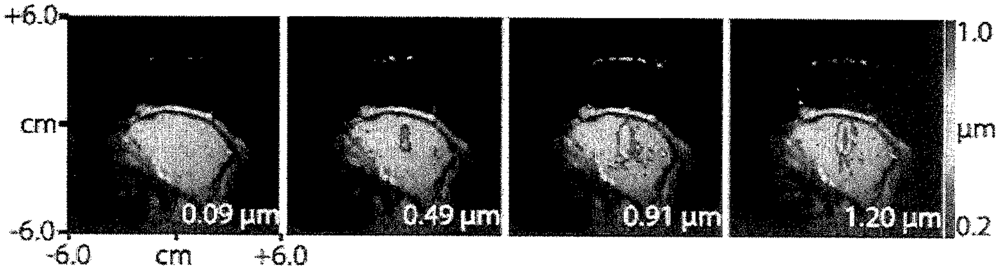
FIGS. 5A-5B are drawings illustrating transcranial displacement images in a living macaque.
Figure 5B:
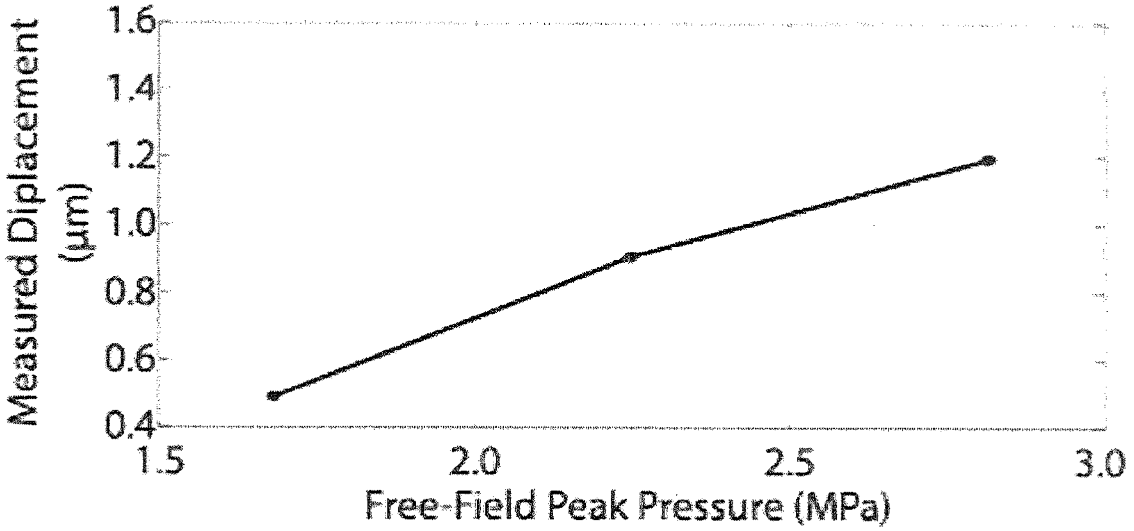

MR-ARFI in non-human primate brain. FIGS. 5A-5B are drawings illustrating transcranial displacement images in a living macaque. FIG. 5A illustrates displacement images obtained with the an optically tracked MR-ARFI pulse sequence in vivo, and the peak transcranial displacement is plotted in FIG. 5B. The measured displacement increased with increasing pressure. At the lowest pressure tested (estimated 0.54 MPa in the brain), a 0.49 μm displacement was obtained. That demonstrates that detectable displacement is feasible at pressures that are not expected to generate cavitation in the brain.

Figure 6:
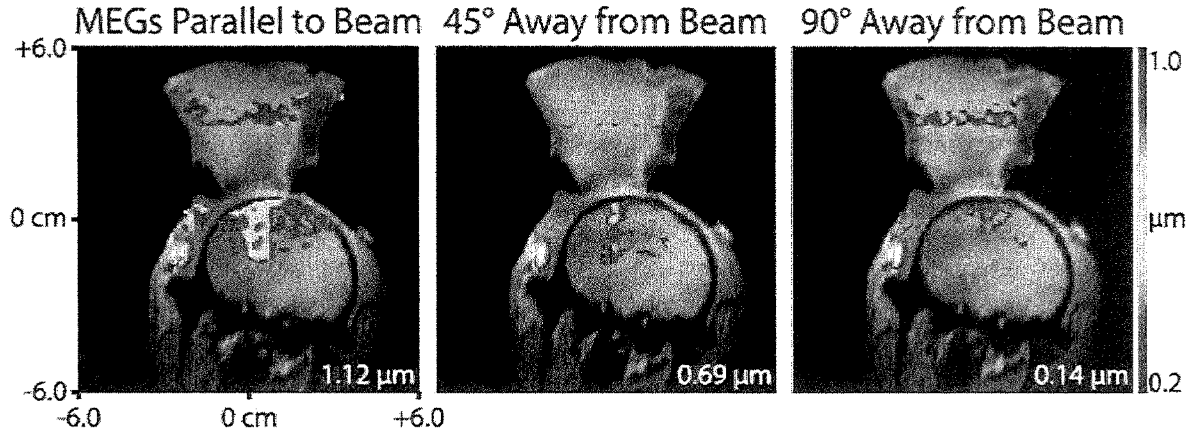
FIG. 6 is a drawing illustrating optical tracking-based alignment of MR-ARFI MEGs with the FUS propagation direction in vivo. Displacement images were acquired with the MEGs aligned parallel to the beam (left side of FIG. 6), 45° away from the beam (middle of FIG. 6), and away from the beam (right side of FIG. 6)

More specifically, FIG. 5 shows transcranial displacement images acquired using the inventors' optically tracked MR-ARFI pulse sequence in a living macaque. The inventors measured a mean focal displacement of 1.20 μm at the highest acoustic power that was applied, which corresponds to a de-rated peak negative pressure (PNP) of 0.90 MPa in the brain (free-field PNP=2.81 MPa). Using the MEG orientation determined by optical tracking, the inventors reduced the power and measured decreasing displacement values to estimate the detection threshold during in vivo imaging with MR-ARFI. The smallest displacement the inventors detected was 0.49 μm at a power level generating a de-rated PNP of 0.54 MPa in the brain (free-field PNP=1.68 MPa). The inventors acquired additional displacement images in one living macaque with the MEGs oriented away from the FUS propagation axis and a de-rated PNP of 0.72 MPa (free-field PNP=2.25 MPa), which are shown in FIG. 6. With the gradients rotated off-axis, the mean focal displacement decreased from 1.12 μm (parallel to the beam) to 0.69 μm (45° away from the beam) and 0.14 μm (90° away from the beam).

FIG. 6 is a drawing illustrating optical tracking-based alignment of MR-ARFI MEGs with the FUS propagation direction in vivo. Displacement images were acquired with the MEGs aligned parallel to the beam (left side of FIG. 6), 45° away from the beam (middle of FIG. 6), and 90° away from the beam (right side of FIG. 6). When the MEGs were prescribed off-axis, the measured displacement reduced, indicating that MR-ARFI in living subjects requires proper MEG alignment to achieve optimal sensitivity to displacement.

Figure 7A:
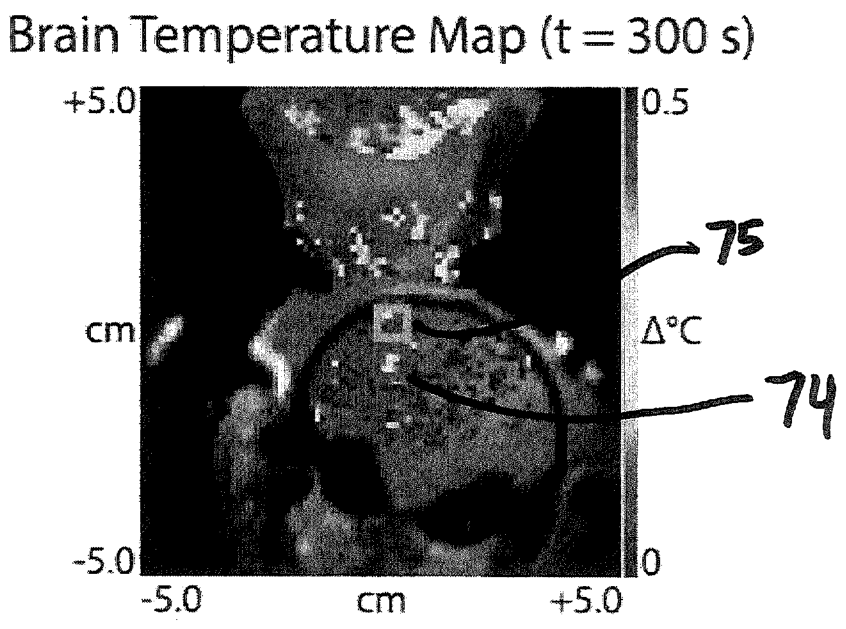
FIGS. 7A-7B are drawings illustrating MR thermometry in a living macaque using MR-ARFI-based acoustic parameters.

A representative brain temperature image acquired in one living macaque at a de-rated PNP of 0.72 MPa (free-field PNP=2.25 MPa) is shown in FIG. 7A. A plot of the mean focal temperature is shown in in red in FIG. 7B and the mean temperature near the skull is in green. These results indicate that no significant brain temperature rise could be detected at the focus via MRI-based temperature monitoring when acoustic parameters designed for MR-ARFI were used. In the brain near the skull the inventors detected approximately a 0.2 °C rise. The inventors did not observe macroscopic evidence of cavitation-induced skin lesions in either monkey in the region where the FUS entered the skull.

Figure 7B:
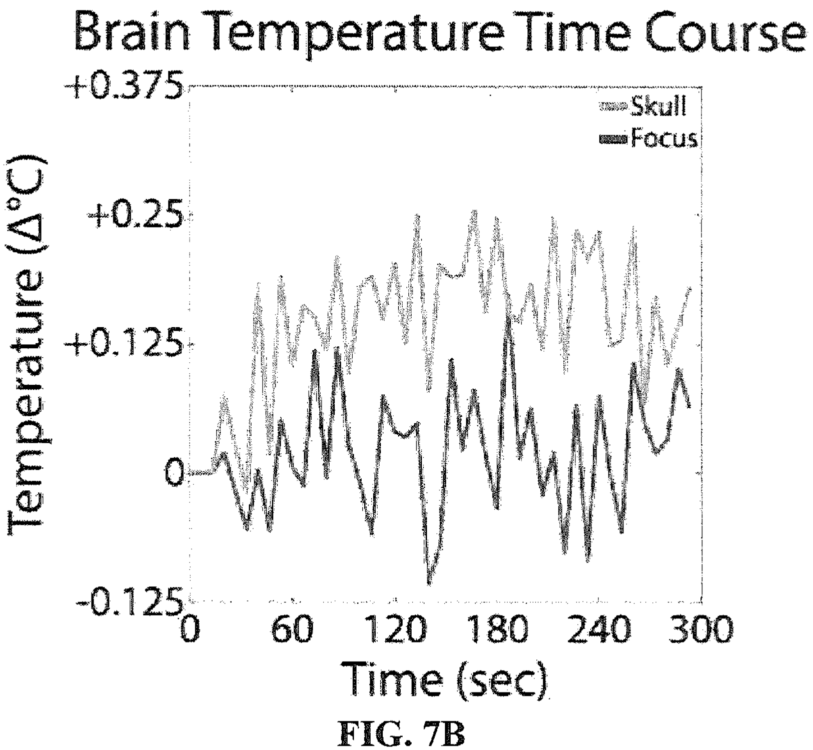

FIGS. 7A-7B are drawings illustrating MR thermometry in a living macaque using MR-ARFI-based acoustic parameters. FIG. 7A illustrates a representative in vivo brain temperature map that shows that no significant temperature rise could be detected using acoustic parameters designed for MR-ARFI. FIG. 7B illustrates the brain temperature time course map at the acoustic focus 74 (see FIG. 7A) and near the skull 75 (see FIG. 7A). Mean focal temperature was computed in a 3×3 px ROI.

Discussion

MR-ARFI in the non-human primate brain. Through simulation and phantom studies, the inventors identified FUS parameters that can be used to transcranially induce displacements in brain tissue and developed methods to measure this displacement with MR-ARFI. The inventors used this system to non-invasively localize the focus of a therapeutic FUS transducer by measuring ARF-induced displacements within a 4-minute scan time in living macaque brains at 7 T MRI. The inventors' work demonstrates the feasibility of using MR-ARFI to map the FUS beam transcranially in a large animal and localize its focus in conjunction with structural imaging-based neuronavigation via optical tracking. Much prior work has established MR-ARFI in phantoms; the inventors' study demonstrates transcranial MR-ARFI in a survival imaging session in the brain of a large animal with intact skull with surrounding tissues of skin, soft tissue, and muscle. In implementing this imaging protocol, the inventors also highlight important design aspects that must be considered when developing transcranial MR-ARFI protocols in large living animals and eventually humans.

Measuring in vivo displacement using MR-ARFI with negligible heating. During the MR-ARFI sequence, a low duty cycle (e.g. long TR and short FUS pulse) was required to avoid heating that could lead to adverse bioeffects in the brain, the skull, and the scalp. In the inventors' study, the inventors minimized heating by using the lowest FUS intensity and shortest pulse duration needed to generate detectable displacement and separating the FUS pulses in time with a TR of 1 second (overall duty cycle of 0.23%). The TR must be short enough to acquire a displacement map in a practical time frame. While tissue damage can occur with large temperature changes it is possible that even small temperature changes in the brain can change neurological function temporally, which would be undesirable during neuromodulation studies. In the inventors' study, heating in the brain was less than ~0.1 °C in MR thermometry images derived from phase maps acquired during MR-ARFI, which is consistent with simulations. In the skull, the inventors' simulations predicted that a ~2 °C temperature rise may be possible. With proper consideration of duty cycle, the inventors' study shows displacement maps in the brain can be generated in a feasible scan time (<5 minutes) with <0.1 °C heating.

To minimize thermal bioeffects, the Food and Drug Administration (FDA) mandates safety limits on the acoustic output levels of clinical ultrasound transducers. The spatial peak-temporally averaged intensity ($I_{SPTA}$), which gauges the likelihood of heating, should not exceed 720 mW $cm^{-2}$. Although those metrics are designed around imaging transducers and pulses, they provide a basic guideline. The pulsing scheme used in the inventors' implementation of MR-ARFI is lower than these limits for diagnostic imaging. Combined with the inventors' simulations and the absence of detectable heating with MR thermometry, the inventors conclude that heating from ARFI pulses can be reduced to a negligible amount while generating high quality images.

Simulated peak negative pressure within and near the skull. The inventors' study suggests that high peak negative pressures that form at the surface and potentially within the skull present the highest risk of potential bioeffects during MR-ARFI. Cavitation is the process of bubbles forming from small gaseous nuclei and subsequently collapsing, generating forces capable of severely damaging tissue. The inventors' retrospective simulation of an FUS pulse with intensity required to produce an approximate 1 μm displacement through the skull show pressures as high as 3.2 MPa (MI~3.5) within or at the surface of the skull, suggesting that cavitation within or near the skull is a realistic concern. The inventors note that their simulations do not encapsulate all possible acoustic interactions, and specifically may be inaccurate within the skull where their CT voxel size is too large to represent microstructure. A prior study of FUS interactions with the microstructure of the skull show that wavelength size heterogeneities can cause internal scattering and shear absorption that may ultimately reduce the PNP within the skull and reflect less uniformly than the inventors' simulations suggest. Additionally, simulations have been shown to underestimate the pressure beyond the skull if the simulation grid spacing is not at least 20 times the wavelength due to a staircasing effect of the skull geometry. The inventors' hydrophone measurements acquired in a water bath compare favorably with simulations, but error associated with staircasing or inability to represent microstructure remain challenging. While no evidence of cavitation-induced skin damage was observed in either monkey on a macroscopic scale, tissue samples will be collected for further pathological analysis at the conclusion of the inventors' neuromodulation experiments.

Cavitation is a stochastic process that is difficult to predict, since it depends on many conditions (presence of cavitation nuclei, frequency and pressure). The probability of cavitation is proportional to the peak negative pressure and inversely proportional to the frequency. During diagnostic ultrasound imaging, the MI is used to gauge the likelihood of cavitation activity and is defined as the peak negative pressure (PNP) in MPa divided by the square root of the center frequency in MHz; it should not exceed 1.9 during shot pulses used during diagnostic ultrasound. Most safety studies for ultrasound have been performed for imaging pulses which generally have higher frequency and use shorter pulses compared to MR-ARFI pulses. Cavitation-induced damage could be more likely when using millisecond-long pulses as required for ARFI, since these pulses provide repeated negative pressure cycles that would potentially drive bubble oscillation and generate repeated cavitation events. The maximum MI of all de-rated FUS pulses in the brain used in the inventors' study (estimated from hydrophone measurements with re-hydrated ex vivo skull) was 1.0. The free-field pressures exceed limits on MI for imaging, which, combined with known subject-to-subject variations in skull attenuation, approaches regimes where cavitation is possible.

Magnitude of the ARF-induced displacement. The inventors detected displacements with magnitude less than 1 μm, which is consistent with other reports of MR-ARFI in living animals. It is helpful to consider the inventors' detected displacement in the context of direct observations of displacement due to radiation force. A majority of analysis of the magnitude of ARF-induced displacement has been done at frequencies greater than 2 MHz to understand displacements during ultrasound imaging-based ARFI; however, rough comparisons can be made to the 802 kHz pulses in the inventors' study since the radiation force is proportional to absorption and scales with frequency:

$$F_{rad} \propto \frac{\alpha I_{sppa}}{c},$$

where α is the absorption of the medium, I is the spatial peak average intensity of the ultrasound pulse, and c is the speed of sound in the medium. One study has used high-speed microscopy to directly observe displacement of a microbead due to acoustic radiation force in a tissue-like phantom, measuring a displacement of 80 μm in response to a 5 MHz pulse (reported $I_{sppa}$=2500 W/cm 2, and MI=1.8). In the inventors' study, the $I_{sppa}$ was approximately 185 W/cm 2 with a center frequency of 802 kHz. Since the intensity and frequency (and hence attenuation) in their study are both approximately 10× lower than the direct observation study, the inventors expect radiation forces in their study to be two orders of magnitude lower. Assuming that micron-scale displacements follow Hooke's law so that force is proportional to displacement, the inventors' observed displacement of 1 μm is expected.

Error in the optically tracked location and angle of the FUS beam can lead to reduced measured displacement and error in slice selection. In previous work, the inventors estimated that optical tracking could localize the acoustic focus with an accuracy of approximately 3 mm with an estimated error of 1.4 degrees in angulation. For small errors in angle, the measured displacement will have nearly full amplitude. Because ARF-induced displacement decreases with increasing distance from the focus, slices must be selected that encompass the beam. In the inventors' study, the angle and location provided by optical tracking guided slice selection, which reduces overall FUS exposure since each MR-ARFI slice requires multiple FUS bursts.

Imaging time, gradient strength, and minimizing FUS exposure. Localizing the ultrasound focus with MR-ARFI should ideally deposit as little FUS energy as possible. Maximizing sensitivity of the MR sequence allows for detection of smaller displacements for a fixed acoustic intensity. To encode micron-scale displacements, MEGs with high gradient strengths and long durations are required to accrue detectable phase shifts into the reconstructed MR-ARFI displacement image. To maximize sensitivity to the ARF-induced phase change, MR-ARFI is typically implemented by complex phase subtraction of two spin echo MR acquisitions obtained with switched polarity MEGs. Additional subtraction of an acquisition without ultrasound application has been shown to minimize motion-induced phase contributions unrelated to the ARF (e.g., respiration). Echo-planar imaging (EPI)-based sequences have also been used to rapidly encode displacement images while minimizing ultrasound energy deposition. In this work, the inventors further developed the MR-ARFI pulse sequence using an optical tracking system to predict the transducer orientation so that the MR-ARFI MEGs could be prescribed along the FUS propagation axis and the slice could be located at the predicted focus. The inventors showed in tissue-mimicking brain phantoms (FIG. 4) and living macaques (FIG. 6) that knowledge of the transducer orientation can improve displacement sensitivity without requiring any additional sonications. In the inventors' experience, a spin echo multi-shot EPI acquisition strategy provided the best balance between scan time and image quality for their application. Previous efforts in MR-ARFI pulse sequence development might be considered for future directions. Both single-shot EPI and steady-state free precession pulse sequences have been proposed to further reduce scan time for MR-ARFI, though these acquisitions are highly sensitive to geometric distortions, especially at 7 T. Encoding schemes that use bipolar gradients or alternating triggers to the transducer (i.e., triggering the sonication on either the forward gradient or the gradient rewinder) have also been shown to improve phase stability. Volumetric imaging strategies for MR-ARFI have also been proposed. A custom surface coil was used for transmit/receive due to the lack of an integrated body/volume coil in the inventors' 7.0 Tesla MRI scanner. The inventors fabricated a 6 cm surface coil integrated with the transducer's coupling cone specifically for this imaging application so that the SNR would be maximized near the acoustic focus in the desired target location of the non-human primate subjects. In the inventors' in vivo MR-ARFI acquisitions, the inventors obtained an SNR of 14.94 (where SNR=peak focal displacement/STD of noise displacement), which was sufficient to clearly observe the acoustic focus in vivo.

Propagation direction, frequency, and f-number. Moderately focused spherical cap transducers are typically used during FUS neuromodulation studies, opposed to hemispherical arrays used during ablation. A moderately focused transducer, as used in the inventors' study, generates an acoustic radiation force primarily in the propagation direction, and similar approaches may not be feasible with hemispherical arrays which would generate increased PNP that does not contribute to the ARF in the direction perpendicular to MEGs but would contribute to both thermal and cavitation-related bioeffects. However, non-linearities (e.g. increased peak pressures) build at the focus more easily with moderately focused transducers compared to hemispheres. Center frequency is another important consideration. Increased center frequencies generate greater force due to increased absorption, while neuromodulation literature suggests that lower frequencies elicit neural responses at lower pressures. A center frequency capable of both MR-ARFI and neuromodulation would be ideal, but a trade-off is required between the abilities to focus through the skull, elicit neuromodulation and displace tissue by a detectable amount. In this study, the inventors used a transducer with multiple resonance peaks so that ARFI was performed at a high frequency while neuromodulation could be performed at a lower frequency without changing the transducer position. To precisely map the neuromodulation beam, further considerations would need to be made about skull interactions at the different frequencies.

Conclusion

This work has demonstrated that MR-ARFI can be used to map and localize a neuromodulation ultrasound beam in the living brain with no detectable negative bioeffects in 5 minutes. The inventors' associated simulations and analysis highlight parameters that should be considered in designing MR-ARFI for minimal FUS exposure. Further optimization of the MR sequence will allow for lower ultrasound intensities and durations to be used which will lower risk of damage and remove confounding factors for research studies. This work describes a method to visualize the acoustic beam in the skull, which will directly benefit the field of FUS neuromodulation and drug delivery.

Materials and Methods

Characterizing transcranial focused ultrasound. A spherically-focused, single-element piezoceramic transducer was used for all experiments (H115MR, Sonic Concepts, Bothell, WA). It has a geometric focus of 63.2 mm and opening diameter of 64 mm. Sonications were performed at its third harmonic of 802 kHz. A custom 3D printed coupling cone with a 3 cm aperture held the transducer. Acoustic data were collected with a needle hydrophone (HNC 0400, Onda Corp., Sunnyvale CA). The free-field pressure from the FUS transducer was measured for a series of input voltages up to a mechanical index (MI) of 1.2. A calibration curve was determined from that data set which was used to estimate pressures used for MR-ARFI.

To estimate the attenuation induced by the NHP skull, the inventors measured the pressure field behind a rehydrated ex vivo macaque skull piece. The skull piece is from the top of the head and is approximately 7×6×3 cm in dimension with a thickness between 2 and 3 mm. The skull piece was placed in degassed water for 24 hours prior to the measurements. The FUS transducer was coupled to a water tank through an acoustic window, and the needle hydrophone's voltage was recorded with the transducer driven at 802 kHz. The pressure during transcranial sonications was then measured at the free-field focal location for 5 different positions of the skull to account for variations in thickness and incident angle. The transmission percentage was taken to be the ratio of pressure measured with and without the skull present.

That transmission percentage was used to derate the inventors' free field pressure values to estimate the focal pressure within the skull.

Acoustic and thermal simulations of ARFI pulses. A numerical model of an NHP skull surrounded by brain tissue was built using the k-Wave package for pressure and thermal simulations. A CT scan of the ex vivo NHP skull fragment was acquired on a clinical PET/CT scanner (Philips Vereos PET/CT, Philips Healthcare, Best, NL). The skull was placed in degassed water for 48 hours and then embedded in 1% agar. The scans were collected at 140 kVp and 300 mAs and had a resolution of $0.19\times0.19\times0.67$ mm$^3$. The images were reconstructed with soft tissue (filter type 'B') and bone (filter type 'YC') filters. The image volume was resampled using the imresize3 function in MATLAB (Mathworks, Natick, MA, USA) to isotropic 0.3 mm voxels. Both the soft tissue and bone CT reconstructions were in Hounsfield units (HU). A histogram with 400 bins of size approximately 7 HU (which varied depending on initial HU minimum and maximum values) was generated. A maximum HU value to be used was determined from the histogram data based on the HU value of the highest bin with at least 500 voxels. This method was used so that the resulting density and speed of sound maps had values similar to previously reported values. The CT data was then compressed so that all values below 0 HU were mapped to 0 HU and all values above the maximum threshold were remapped to that value (1632 HU for the bone reconstruction filter). The soft tissue filter was used to generate a mask of the skull fragment to apply acoustic absorption, thermal conductivity, and specific heat in the simulations (see Table 1 below). Other acoustic properties were generated from the CT images reconstructed with the bone filter using a method similar to Aubry et al. The porosity was estimated for each voxel as ($\varphi_i=1-(HU_i/\max(HU_{volume})$)). That value was then used to calculate a speed of sound and density for each voxel $\rho_i=\varphi*\rho_{water}(1-\varphi)*\rho_{bone}$; $c_i=(c_{Max}-c_{Min})*(1-\varphi)+c_{Min}$ where $\rho_{water}=1000$ kg·m$^{-3}$, $\rho_{bone}=2100$ kg·m$^{-3}$, cam, $=1500$ m·s$^{-1}$, and $c_{max}=2900$ m·s$^{-1}$. All parameter maps were padded to a grid size of [Nx,Ny,Nz]=[300,280,280].

TABLE 1

Thermal parameters and acoustic absorption values for the skull and the rest of the simulation grid.

| Parameter | Skull | Grid |
|---|---|---|
| Absorption (dB/cm/MHz) | 8 | 0.4 |
| Thermal Conductivity (W/m/K) | 0.3 | 0.5 |
| Specific Heat (J/kg/K) | 1700 | 3600 |

The H115MR transducer was modeled in k-Wave and placed so that the geometric focus was approximately 1 cm past the inner surface of the skull fragment. Thermal simulations presented in this paper represent a retrospective simulation of the inventors' in vivo experiments. An 80-cycle pulse was used as the input source for the transducer. The amplitude was matched so that a free-field simulation was the same as the highest estimated free-field pressure used in vivo (methods described below). An additional pressure simulation was performed to compare the inventors' simulation results with their water tank measurements behind the skull fragment. For this simulation the free field pressure was matched to the measured free field pressure in the water tank (284 kPa) and then a simulation was performed through the skull to simulate the transmission loss in a water tank. A GPU-accelerated 3D k-Wave simulation was run on a workstation PC (HP Z820, Xeon E5, with 256 GB RAM, Hewlett Packard, Palo Alto, CA) with a 16 GB Nvidia Titan GPU (Nvidia, Santa Clara, CA). The maximum pressure was recorded for every voxel in the simulation grid.

Heating predictions were made by solving the Pennes' bioheat equation as implemented in the k-Wave package. The maximum pressure and acoustic absorption from the pressure simulation were used to scale the volume rate of heat deposition for the bioheat simulation. This simulation implemented the bioheat equations in a region around the focus that contained the part of the skull fragment that most of the sound passed through (a grid size of [Nx,Ny,Nz]=[140,80,80] with 0.3 mm spacing in all dimensions). The simulated ARFI pulse duration and duty cycle was matched to that used during MR-ARFI (4.5 ms pulses with a 1 Hz pulse repetition frequency (PRF)). A time step of 0.1 ms was used during the 4.5 ms ARFI pulses, while a longer time step of 5 ms was used during the "off" periods to ensure feasible computation time. 100 sonications were simulated and the temperature was recorded at each point in the grid for each time point.

MR-ARFI pulse sequence. All MR imaging was performed on a 7.0 T Philips Achieva human research scanner (Philips Healthcare, Best, NL). Displacement images were acquired using an optically tracked 2D spin echo MR-ARFI pulse sequence. Unipolar trapezoidal motion-encoding gradients (MEGs) were placed before and after the refocusing RF pulse to generate ARFI contrast. The MEGs were set to 3 ms in duration with the scanner's maximum gradient strength (40 mT·m$^{-1}$) on their plateaus, which resulted in low diffusion-weighting (b-value≈9.3 s·mm$^{-1}$). Imaging parameters were: 12.0×12.0 cm 2 FOV; 60×60 matrix; 2.0×2.0 mm$^2$ voxel size; 1 slice; 2.0 mm slice thickness; echo time (TE)/repetition time (TR) 17/1000 ms; 2D multi-shot echo-planar imaging (EPI) readout with 5 lines per TR. A custom 6 cm surface coil integrated with the transducer's coupling cone was used for transmit/receive. In each TR, a TTL pulse was sent from the scanner to the FUS waveform generator to trigger a sonication. Sonications were synchronized with the rewinder MEG using a trigger offset of −2 ms to allow displacement to reach a steady state. Sonications were performed at 802 kHz for 4.5 ms (3609 cycles) with an acoustic pressure (maximum free field of 2.81 MPa) that would not be expected to exceed a temperature increase greater than 1 °C or MI greater than 1.1 within the brain based on the previously described acoustic simulations and hydrophone experiments. Four phase images with switched polarity MEGs and with or without a sonication were acquired in an interleaved fashion ($\varphi^{ON+}$, $\varphi^{OFF+}$, $\varphi^{ON-}$, $\varphi^{OFF-}$). Each phase image was acquired with five averages. Since the ultrasound PRF is specified by the TR of the pulse sequence, the inventors used a relatively long TR of 1000 ms (1 Hz PRF) to maintain a low duty cycle. In total, 120 sonications were performed at a duty cycle of 0.23%, with a total scan time of 4.0 minutes to produce one displacement image. Displacement images were reconstructed using complex phase subtraction $$(\Delta x=\angle(\phi^{ON+}\cdot(\phi^{ON-})^{*}\cdot(\phi^{OFF+}\cdot(\phi^{OFF-})^{*})^{*})/2\gamma G\tau,$$

where γ is the gyromagnetic ratio, G is the gradient strength, and τ is the gradient duration). Images were reconstructed offline in MATLAB 2017a (MathWorks, Natick, MA).

Since the transducer is freely-movable and manually positioned over the targeted region, prescribing the MEGs for MR-ARFI requires precise knowledge of the slice offset and angulation of the transducer along the anterior-posterior (AP or ±x), right-left (RL or ±y), and superior-inferior (SI or ±z) cardinal axes. The inventors used optical tracking to ensure that the MEGs were aligned with the FUS propagation direction and that the imaged slice was prescribed at the optically tracked location of the acoustic focus. Previous efforts have described how optical tracking can be used to estimate the focus location and target the FUS beam. This procedure uses a Polaris Vicra optical tracking system (Northern Digital Inc., Ontario, CAN) and is illustrated in FIG. 3. An MM-compatible rigid body tracker is mounted to the patient bed and serves as the global reference location. Another body tracker is mounted to the transducer as the tracked location. Multimodality fiducial markers (IZI Medical Products, Maryland, USA) are placed near the focus location. The fiducials are localized in image space using a 3D fast spoiled gradient-recalled echo T1-weighted high-resolution isotropic volume examination (THRIVE) pulse sequence (voxel size 0.4×0.4×1 $mm^3$, TE/TR 1.89 ms/4 ms). The fiducials are manually identified in the T1-weighted image stack using 3DSlicer (http://www.slicer.org/). In front of the optical tracking camera, the fiducials are localized in physical space using a reflective positioning stylus and recorded in 3DSlicer. Finally, these are registered to the fiducials' image locations, yielding a physical-to-image space transform. The transducer can then be freely rotated in physical space, with 3DSlicer reporting the slice offset and angulation required to prescribe the MR-ARFI scan with maximum displacement sensitivity.

Optically tracked MR-ARFI in phantoms with simulated targeting. To simulate the targeting of arbitrary brain regions with the inventors' optically tracked MR-ARFI pulse sequence, and to demonstrate the need to align the MR-ARFI MEGs with the FUS propagation direction via optical tracking, displacement images were acquired in an ex vivo agarose phantom designed to mimic brain tissue acoustic properties (1% agarose, 4% graphite, and 10% n-propanol in water). Gel based phantoms typically have a lower limit for stiffness around 10 kPa while brain tissue is much lower near 1 kPa. Based on this difference, the inventors do not expect the relative magnitudes of ARF-induced displacement in brain tissue and this phantom to be comparable, and thus do not compare the magnitude of displacement of the phantoms to tissue. For these experiments, the transducer housing was rigidly attached to a cylindrical phantom mold, and the transducer-phantom apparatus was mounted on a plastic tabletop with a three-axis stereotactic frame. In this way, sonications could be targeted in any physical orientation. Targeting of the transducer-phantom apparatus is demonstrated in FIG. 3B and FIG. 3C. To fabricate the phantom, grams of food-grade agarose powder was added to a 450 mL beaker of cold water. The beaker was heated in a microwave until it boiled. Twenty grams of 400 grit graphite powder (Panadyne Inc, Montgomeryville, PA) was then added, and after about 5 minutes of cooling, 50 mL of n-propanol was added to the agarose-graphite phantom mixture. The transducer housing was partially filled with 1% agarose in water and allowed to set before the phantom mixture was poured into the housing and phantom mold.

Displacement images were acquired using the inventors' optically tracked MR-ARFI pulse sequence after translating and rotating the transducer to a slice offset and angulation about the AP, RL, and/or SI cardinal axes. The transducer was positioned in one of six physical orientations: No rotation; 29° about SI only; 48° about SI only; 21° about RL only; 30° about SI and 25° about RL; and 34° about SI and 19° about RL. Four displacement images were acquired per transducer orientation: MEGs aligned along AP only; RL only; SI only; and aligned with the FUS propagation axis as determined by optical tracking.

Optically tracked MR-ARFI in living non-human primates. Two healthy adult female macaque monkeys (*M fascicularis*) were scanned with the approval of the Institutional Animal Care and Use Committee (IACUC) at Vanderbilt University and in accordance with all relevant guidelines and regulations. For these experiments, a previously developed experimental platform for targeted ultrasonic neuromodulation in non-human primates was used. Animals were sedated and positioned in a three-axis stereotactic frame with consistent physiological monitoring for the duration of the experiments. The location of the FUS beam was first determined using the same optical tracking workflow performed for the inventors' phantom experiments. This information was used to target the transducer on the right somatosensory network (S1 areas 3*a*/3*b*). Transcranial displacement images were acquired with the inventors' optically tracked MR-ARFI pulse sequence, ensuring that the MEGs were aligned with the FUS propagation direction and with the imaged slice prescribed at the optically tracked location of the acoustic focus. In one living macaque, the inventors acquired additional displacement images aligned with the beam but with the acoustic pressure reduced by 20% and 40%, to provide an estimate of displacement sensitivity at low acoustic powers. As a negative control, the inventors also acquired displacement images in one living macaque with the MEGs oriented off axis (i.e., 45° and 90° away from the FUS propagation direction).

Stereotactic Frame for Repeated Transcranial Therapy

Figure 8:
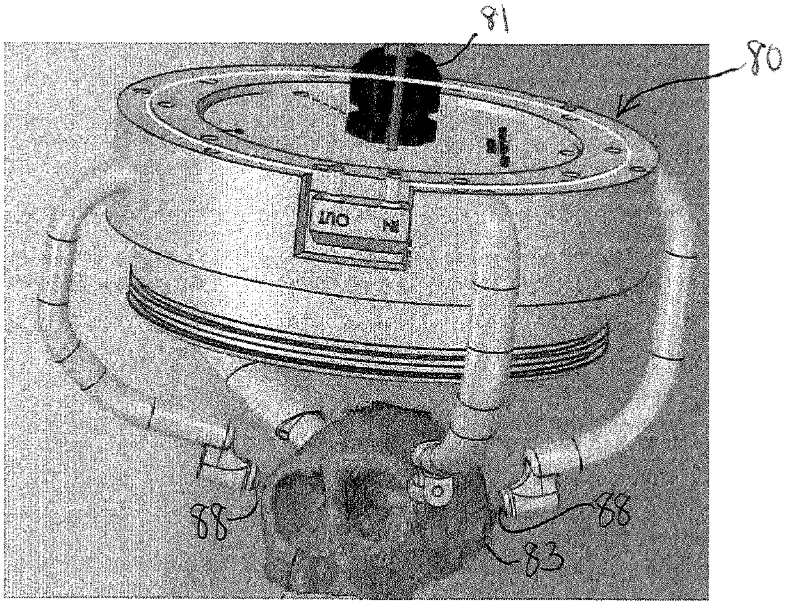
FIG. 8 is a drawing illustrating a platform spatially fixing the therapeutic transducer to a macaque skull through bone anchor screws.

Transcranial focused ultrasound (FUS) is being explored for many neural applications, as it is non-invasive and can target the brain in mm-scale. With MR guidance, the focus can be visualized and steered, but performing procedures within the MM is costly and challenging. Not all procedures require close monitoring and the ability to repeatedly apply FUS to the same location may be desirable in applications such as neuromodulation or drug delivery. To address this need, the inventors developed and characterized a minimally invasive platform (stereotactic frame) 80 (see FIG. 8) using skull anchor screws 88 that allows for precise and repeatable transcranial FUS treatment without the need for MR-guidance following an initial calibration scan. In particular, FIG. 8 is a drawing illustrating a platform 80 spatially fixing the therapeutic transducer 81 to a macaque skull 83 through bone anchor screws 88.

The stereotactic frame for repeated transcranial therapy described in any of the embodiments above may or may not be patient-specific. The following example describes a patient-specific embodiment of the stereotactic frame for repeated transcranial therapy.

Why Transcranial Stereotactic FUS?

This technique may be used to treat a variety of neurological disorders such as essential tremor, tremors related to Parkinson's disease, depression, neuropathic pain, obsessive-compulsive disorder, dyskinesia related to Parkinson's disease, and Alzheimer's disease.

Some specific implementations of transcranial stereotactic FUS include:

Ablation (ExAblate, Neuro)

MRgFUS

Lower intensity treatments

Reversible stimulation for pain management

Treat same region repeatedly

Transcranial stereotactic FUS

Rigid, removable, frame joining cranium and transducer

No MR guidance necessary after initial image session

Transcranial FUS is approved for treating essential tremors. The ExAblate, current main tool, relies on MR guidance for the ablation of relevant tissue. However, for things such as pain management, where less aggressive but more frequent stimulation is desired, use of MR guidance every time may not be economically viable. A stereotactic frame that can directly lock and link the transducer and patient cranium into place, in the same manner every single time, would allow for continued treatment without MR guidance after the initial scan session. Ablation (ExAblate, Neuro).

Designing/Building a Custom (i.e., Patient-Specific) Frame

The following components were used to design/build a custom frame such as the frame depicted in FIG. 8.

5 mm WayPoint™ anchors, FHC

Cranial Vault Explorer (CRAVE), Vanderbilt University 128-element custom therapeutic transducer Skull overlayed with NHP-MRI to approximate thalamus target Focus assessed via MR-thermometry in 7T In short, to design the platform (using the above components), Waypoint Anchors were first placed into a macaque skull. Its CT was then acquired and Cranial Vault Explorer was used to extract the anchor location and orientation. The information was then loaded into a CAD program, where a frame securing the therapeutic transducer to the anchors was employed (see FIG. 8). Anatomical or functional maps of brain activity can be overlayed on the skull to approximate a target coordinate to aim for. To test the setup and localize the focus, the inventors filled the skull with phantom material and conducted MR-thermometry. The data was then imported into CRAVE™ for analysis.

As more fully explained, 5 mm anchors (Waypoint™, FHC) were positioned and screwed into a macaque skull, and a CT was obtained. Using the CT for anatomical guidance, a platform accommodating a custom 128-element therapeutic transducer was designed using the Cranial Vault Explorer (CRAVE) software, 3D printed and affixed with MR/CT fiducials. Platform accuracy was tested on an agar-graphite-filled skull phantom/platform/transducer ensemble (FIG. 8), where FUS was steered into the phantom and the focus was localized through MR-acoustic radiation force imaging. Data was processed in MATLAB, imported into CRAVE and co-registered to CT-space. The position with highest displacement in the ARFI maps was taken as the focal center. Manual co-registration error was characterized by repeatedly importing and registering the same scan and assessing deviations in the focal center. To assess repeatability between therapies, the FUS focus was acquired and compared over multiple ensemble assemblies.

Manual registration error was minimal, at 0.1 mm in both axial and lateral deviation. Co-registering data acquired over 3 separate ensemble assemblies, the inventors observed good agreement in focal position, with standard deviations in the axial, x and y dimensions of 1.5, 0.2 and 0.9 mm, respectively. The inventors' preliminary platform model shows promise as a therapeutic tool, as it reliably reached the same location between assemblies, with deviations similar or smaller than the free-field focus size (9.3 and 2.2 mm in axial and lateral, respectively).

Figure 9A:
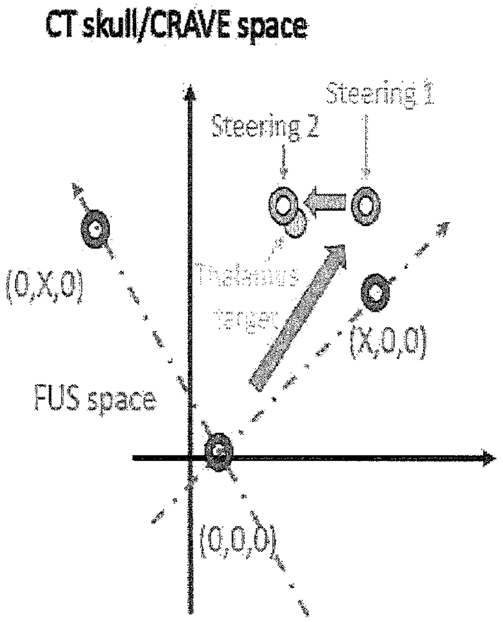
FIG. 9A is a plot illustrating initial setup/acquisition for frame assessment in CT skull/CRAVE space for orienting the FUS transducer.

To test the setup, in CRAVE space, the inventors first found where the unsteered focus fell. The focus was then steered a known amount in each direction to orient the transducer. The inventors calculated an approximate steering coordinate to the target, tested it and modified it. The inventors then, over several scans and days, re-assembled the setup and acquired thermometry data at the unsteered foci and the two steered focus. Steering coordinates were not modified. After initial acquisition, transducer steering coordinates (steering 1, 2, as shown in FIG. 9A) were left constant throughout the demonstration. In particular, FIG. 9A is a plot illustrating initial setup/acquisition for frame assessment in CT skull/CRAVE space for orienting the FUS transducer.

Figure 9B:
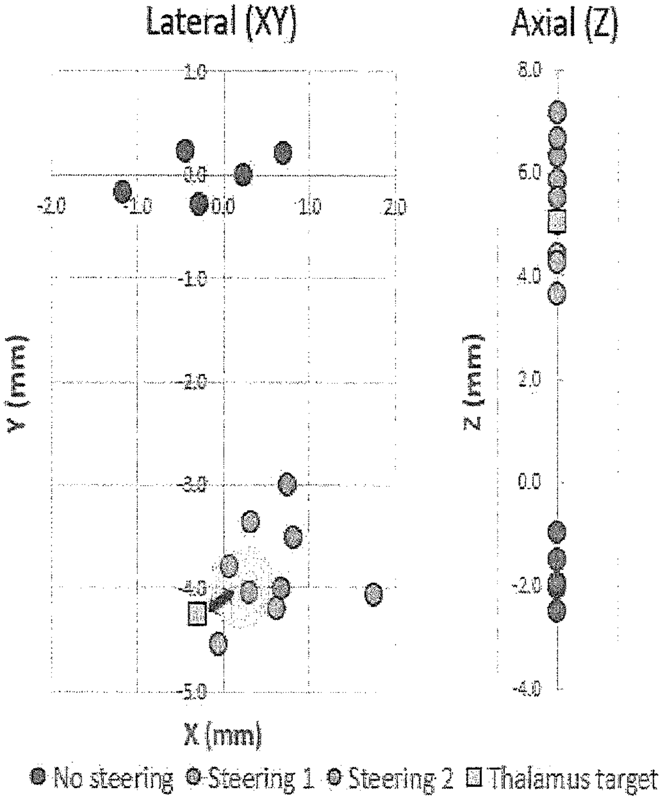
FIG. 9B are lateral and axial plots illustrating the thermometry focus for the CT skull/CRAVE space shown in the plot of FIG. 9A.

FIG. 9B are lateral and axial plots illustrating the thermometry focus for the CT skull/CRAVE space shown in the plot of FIG. 9A. Blue=no steering, Orange=first steering, Grey=walked in focus, and the thalamus target in yellow. Most notably, the focus was able to be steered to within 1 mm of the target, and with sub-mm variation over multiple assemblies. With reference to FIG. 9B, the resultant (Lateral XY, Axial Z) error is as follows:

No steering relative to (0,0,0)
(0.6, 1.8)+/−(0.4, 0.6) mm

Steering 1 relative to target
(1.2, 1.3)+/−(0.6, 0.6) mm

Steering 2 relative to target
(0.7, 0.7)+/−(0.6, 0.3) mm

Conclusions

Overall, the inventors developed a rigid, removable, stereotactic frame for transcranial ultrasound treatment.

Using the frame, the inventors were able to steer the focus to a pre-determined target with sub mm (<1 mm) accuracy, and do this repeatedly over multiple assemblies, i.e., focus was reproducible (without MR-guidance) over multiple assemblies (<1 mm and n=4, for example).

The initial steering orientation, steering, focus verification and steering adjustments can all be done in one imaging session The inventors believe that this is a powerful tool for patients requiring regularly scheduled, repeated transcranial neuromodulation treatments.

In a separate experiment, sonications were performed in one animal using the same acoustic parameters for MR-ARFI, but monitored with an MR thermometry pulse sequence to provide an in vivo estimate on brain temperature changes during MR-ARFI. Temperature images were acquired using a 2D gradient-recalled echo thermometry pulse sequence9. Imaging parameters were: 10.0×10.0 cm 2 FOV; 50×50 matrix; 2.0×2.0 $mm^2$ voxel size; 5 slices; 2.0 mm slice thickness; TE/TR 10/25 ms; 2D single-shot EPI readout. Temperature images were reconstructed in MATLAB using the hybrid multibaseline subtraction and referenceless method.

Example Using Acoustic Signature: A Therapeutic Ultrasound Guidance Technique with Sub-Millimeter Accuracy Background and Motivation Accurate targeting is paramount for transcranial FUS procedures. A method for targeting FUS dubbed acoustic signature is described, which exploits acoustic feedback from a target's unique reflection patterns to guide the transducer to a previously defined orientation. The inventors report the accuracy and validity of using acoustic signatures for targeting in a three degrees-of-freedom (DOF) scenario in a water bath and in an experimental setup appropriate for targeting the brain of a non-human primate (NHP). The newly developed method allows for highly repeatable placement of the ultrasound transducer relative to the skull.

Methods

A 128-element array therapeutic transducer was used for transmitting and receiving sound. A model of an MRI-acquired macaque head was 3D printed and served as the reflective target for experiments. Both phantom and transducer were optically tracked, allowing for the optical validation of the acoustic signature technique accuracy. The phantom was mounted to a 3-axis stage and a custom NHP surgical table for 3- and 5-DOF tests, respectively. The phantom was placed in an initial orientation within the focal zone of the transducer, and the optically tracked locations and acoustic signature of the phantom were recorded. An acoustic signature consisted of pulse echo data received on 11 of the transmit elements distributed around the transducer during 128 sequential transmit signals corresponding to single transmit elements. A custom script was designed such that acoustic acquisitions were repeatedly collected, comparing them with the initial acoustic signature and plotting an error metric in real time representing the similarity.

The inventors characterized the error profile of the acoustic signature method by quantifying the error metric with the phantom at known locations relative to the transducer while in a water bath. To test the positioning accuracy of the technique, the phantom was moved away from the target to an unknown orientation. While recording real-time pulse-echo measurements, the error was minimized by manipulating the orientation of the phantom (3-DOF test) or transducer (5-DOF) which guides the transducer back to the desired target.

Results

In the 3-DOF test, the net targeting error was 0.30+/−0.27 mm with lateral component errors 0.07 and 0.13 mm and axial error 0.20 mm (n=10). In the surgical table 5-DOF test, the targeting error was 2.11+/−0.99 mm with 1.42 and 1.17 mm lateral component errors, 0.71 mm axial error and 3.2+/−2.2° (n=10) summed rotational error. The error profile of the algorithm for all targets tested converges to zero at the target, demonstrating that the accuracy of this technique is limited by the positioning apparatus and not the uniqueness of the acoustic signature. The inventors' method enables highly precise and repeatable FUS alignment for therapies which require multiple FUS sessions at the same target.

Although embodiments are described above with reference to mapping a FUS beam in a patient's head (or skull), employing a patient-specific stereotactic frame anchored between the patient's head, and delivering FUS therapy to the patient's head using the patient-specific stereotactic frame, the patient's head described/employed in any of the above embodiments may alternatively be another body part of the patient. Such alternatives are considered to be within the spirit and scope of the present invention, and may therefore utilize the advantages of the configurations and embodiments described above.

The method steps in any of the embodiments described herein are not restricted to being performed in any particular order. Also, structures or systems mentioned in any of the method embodiments may utilize structures or systems mentioned in any of the device/system embodiments. Such structures or systems may be described in detail with respect to the device/system embodiments only but are applicable to any of the method embodiments.

Features in any of the embodiments described in this disclosure may be employed in combination with features in other embodiments described herein, such combinations are considered to be within the spirit and scope of the present invention.

The contemplated modifications and variations specifically mentioned in this disclosure are considered to be within the spirit and scope of the present invention.

More generally, even though the present disclosure and exemplary embodiments are described above with reference to the examples according to the accompanying drawings, it is to be understood that they are not restricted thereto. Rather, it is apparent to those skilled in the art that the disclosed embodiments can be modified in many ways without departing from the scope of the disclosure herein. Moreover, the terms and descriptions used herein are set forth by way of illustration only and are not meant as limitations. Those skilled in the art will recognize that many variations are possible within the spirit and scope of the disclosure as defined in the following claims, and their equivalents, in which all terms are to be understood in their broadest possible sense unless otherwise indicated.

What is claimed is:

1. A method for applying focused ultrasound (FUS) to a patient, the method comprising:

mapping a FUS beam in the patient inside a magnetic resonance (MR) environment, the mapping employing MR thermometry or MR-acoustic radiation force imaging (MR-ARFI);

obtaining acoustic data during the mapping by recording at least radiofrequency (RF) echo signals resulting from the use of a FUS transducer or an array of FUS transducers positioned inside the MR environment and acoustic feedback from a reflection pattern of the patient as an acoustic signature of FUS transducer position relative to the patient;

building a patient-specific stereotactic frame using the acoustic data obtained from the mapping; and after obtaining the acoustic data inside the MR environment, delivering FUS therapy to the patient outside of the MR environment using the patient-specific stereotactic frame and using the acoustic data, wherein delivering FUS therapy to the patient outside of the MR environment comprises comparing a current acoustic signature obtained outside of the MR environment with the acoustic signature obtained during the mapping inside the MR environment to confirm that the FUS transducer or the array of FUS transducers is positioned relative to the patient in a same orientation as during the mapping.

2. The method of claim 1, wherein:

the mapping of the FUS beam in the patient's head is performed inside the MR environment;

in the building step, the patient-specific stereotactic frame is anchored between the patient's head and the FUS transducer that generates the FUS beam; and in the delivering step, the FUS therapy is delivered to the patient's head using the patient-specific stereotactic frame.

3. The method of claim 1, wherein the mapping step comprises recording a location of the FUS transducer or the array of FUS transducers positioned inside the MR environment relative to the patient.

4. The method of claim 3, wherein the mapping step comprises recording ultrasound parameters.

5. The method of claim 4, wherein the mapping step comprises calculating FUS aberration corrections.

6. The method of claim 4, wherein, in the building step, the data obtained from the mapping comprises the ultrasound parameters.

7. The method of claim 5, wherein, in the building step, the data obtained from the mapping comprises the FUS aberration corrections.

8. A system that applies focused ultrasound (FUS) to a patient, the system comprising:

a patient-specific stereotactic frame configured as being built using acoustic data obtained from mapping of a FUS beam in a patient inside a magnetic resonance (MR) environment, the mapping of the FUS beam in the patient inside the MR environment employing MR thermometry or MR-acoustic radiation force imaging (MR-ARFI), wherein the acoustic data obtained during mapping of the FUS beam in the patient inside the MR environment comprises at least radiofrequency pulse echo signals resulting from the use of a FUS transducer positioned inside the MR environment and acoustic feedback from a reflection pattern of the patient, as a signature of FUS transducer position relative to the patient; and a FUS transducer configured to deliver FUS therapy to the patient outside of the MR environment using the patient-specific stereotactic frame and using the acoustic data, wherein the FUS transducer is further configured to obtain a current acoustic signature outside of the MR environment for comparison with the acoustic signature obtained during the mapping inside the MR environment to confirm that the FUS transducer is positioned relative to the patient in a same orientation as during the mapping;

wherein the patient-specific stereotactic frame is anchored between the patient and the FUS transducer that delivers the FUS therapy outside of the MR environment.

9. The system of claim 8, wherein:

the mapping of the FUS beam is performed in the patient's head inside the MR environment;

the patient-specific stereotactic frame is anchored between the patient's head and the FUS transducer that delivers the FUS therapy; and the FUS transducer is configured to deliver the FUS therapy to the patient's head using the patient-specific stereotactic frame.

10. The system of claim 8, wherein the mapping of the FUS beam in the patient inside the MR environment comprises recording a location of the FUS transducer relative to the patient.

11. The system of claim 10, wherein the mapping of the FUS beam in the patient inside the MR environment comprises recording ultrasound parameters.

12. The system of claim 11, wherein the data obtained from the mapping comprises the ultrasound parameters.

13. The system of claim 11, wherein the mapping of the FUS beam in the patient inside the MR environment comprises calculating FUS aberration corrections.

14. The system of claim 13, wherein the data obtained from the mapping comprises the FUS aberration corrections.

* * * * *